(12) United States Patent
Magnet et al.

(10) Patent No.: US 8,431,645 B2
(45) Date of Patent: Apr. 30, 2013

(54) RIGID-MATRIX COMPOSITION-GRADIENT COPOLYMERS WHICH ARE SOLUBLE AND/OR DISPERSIBLE IN WATER AND IN ORGANIC SOLVENTS

(75) Inventors: Stephanie Magnet, Morlanne (FR); Helene Hediger, Mourenx (FR); Olivier Guerret, La Tour de Salvagny (FR)

(73) Assignee: Arkema France, Colombes (FR)

( * ) Notice: Subject to any disclaimer, the term of this patent is extended or adjusted under 35 U.S.C. 154(b) by 128 days.

(21) Appl. No.: 13/119,056

(22) PCT Filed: Sep. 18, 2009

(86) PCT No.: PCT/FR2009/051760
§ 371 (c)(1), (2), (4) Date: Mar. 15, 2011

(87) PCT Pub. No.: WO2010/031973
PCT Pub. Date: Mar. 25, 2010

(65) Prior Publication Data
US 2011/0172352 A1    Jul. 14, 2011

(30) Foreign Application Priority Data
Sep. 19, 2008 (FR) ..................................... 08 56309

(51) Int. Cl.
*C08F 220/18* (2006.01)
*C08F 2/38* (2006.01)
*C08F 2/00* (2006.01)
*C08F 30/02* (2006.01)
*C08L 33/08* (2006.01)

(52) U.S. Cl.
USPC ...... 524/562; 526/193; 526/318.45; 526/274; 526/335

(58) Field of Classification Search ................. 524/562; 526/193, 318.45, 274, 335
See application file for complete search history.

(56) References Cited

U.S. PATENT DOCUMENTS

| | | |
|---|---|---|
| 2004/0180019 A1 | 9/2004 | Mougin |
| 2005/0107577 A1* | 5/2005 | Couturier et al. ............. 528/310 |
| 2007/0128127 A1 | 6/2007 | Gawtrey et al. |
| 2009/0270559 A1 | 10/2009 | Schmidt et al. |
| 2010/0010103 A1 | 1/2010 | Schmidt et al. |

* cited by examiner

Primary Examiner — William Cheung
(74) Attorney, Agent, or Firm — Millen, White, Zelano & Branigan, P.C.

(57) ABSTRACT

The invention relates to composition-gradient copolymers, comprising:
  repeat units resulting from the polymerization of at least one first monomer $M_1$, the corresponding homopolymer of which exhibits a glass transition temperature $Tg_1$ of less than 20° C., said repeat units representing from 15 to 40% by weight, with respect to the total weight of the copolymer;
  repeat units resulting from the polymerization of at least one second monomer $M_2$, the corresponding homopolymer of which exhibits a glass transition temperature $Tg_2$ of greater than 20° C., said repeat units representing from 45% to 65% by weight, with respect to the total weight of the copolymer;
  hydrophilic repeat units resulting from the polymerization of a least one third monomer $M_3$, said repeat units representing from 10 to 25% by weight, with respect to the total weight of the copolymer.

19 Claims, No Drawings

RIGID-MATRIX COMPOSITION-GRADIENT COPOLYMERS WHICH ARE SOLUBLE AND/OR DISPERSIBLE IN WATER AND IN ORGANIC SOLVENTS

This application is a Nation Stage filing under 35 U.S.C. Section 371 of PCT Application No. PCT/FR2009/051760, filed on Sep. 18, 2009. This application also claims the benefit of France Patent Application No. 0856309, filed Sep. 19, 2008. The entirety of both applications is incorporated hereby reference.

The present invention relates to rigid-matrix composition-gradient copolymers which are soluble and/or dispersible in water and in organic solvents and which are obtained by controlled radical polymerization, said copolymers exhibiting an amphiphilic nature, namely that they exhibit both a hydrophilic part and a hydrophobic part.

The present invention also relates to a process for the preparation of such copolymers and to a process for the aqueous dissolution of these copolymers.

These copolymers have applications in a great variety of fields, in particular fields requiring aqueous dissolution of copolymers of this type, such as the fields of surface treatment, in particular paints or adhesives, or also such as the cosmetics field, and in pigment dispersion.

Thus, the general field of the invention is that of amphiphilic copolymers.

PRIOR STATE OF THE ART

Amphiphilic copolymers are copolymers comprising, in their structure, at least a hydrophilic part resulting from the polymerization of monomers carrying at least one hydrophilic functional group and at least a hydrophobic part resulting from the polymerization of monomers carrying at least one hydrophobic functional group.

These copolymers can be prepared by various polymerization techniques, such as anionic polymerization, conventional radical polymerization or controlled radical polymerization.

The amphiphilic copolymers resulting from conventional radical polymerization are generally random copolymers, some of them being known in particular under the term of ASR (Alkali-Soluble Resin). These copolymers are formed from hydrophobic monomer(s), such as styrene or α-methylstyrene, and hydrophilic monomer(s), such as acrylic acid or methacrylic acid. Mention may be made, among ASRs, of the example of the Joncryl copolymers from Johnson Polymer (styrene-acrylic resins), that of the Neocryl products (styrene-acrylic copolymers) and that of the Haloflex products (vinyl-acrylic copolymers).

The disadvantage of the random copolymers produced by conventional radical polymerization is that they exhibit units distributed nonhomogeneously between the various polymer chains. From this remains the fact that a certain portion of the polymer chains may be very hydrophilic, thus comprising a high proportion of units resulting from the polymerization of hydrophilic monomers, while another portion may be very hydrophobic.

One solution for overcoming the problems inherent in the nonhomogeneity in composition of the polymer chains is to carry out the synthesis of the polymers by controlled radical polymerization. This type of polymerization thus makes it possible to result in copolymers, the chemical compositions of the polymer chains of which are homogeneous and similar from one chain to another.

The amphiphilic copolymers conventionally resulting from controlled radical polymerization are, for the majority, block copolymers, each block of which exhibits specific properties.

However, the processes for the preparation of such copolymers are often lengthy and expensive and call for a multistage synthesis. This is because the preparation of block copolymers involves the sequence of at least two polymerization stages, for the purpose of forming at least two blocks, between which there is inserted a stage of devolatilization of the residual monomers present at the end of the first stage.

Thus, the inventors set themselves the objective of providing composition-gradient copolymers which do not exhibit the problems of nonhomogeneity in composition within the same chain and the problems inherent in the synthesis of block copolymers.

Composition-gradient copolymers comprising two or more different monomers are known, for example, from the document US 2007/0128127, which teaches that a composition comprising from 2 to 25% by weight of a hydrophilic monomer, from 50 to 90% by weight of a monomer with a Tg of less than or equal to 20° C. and from 5 to 25% by weight of an additional monomer is suitable for use in hair treatment by preventing the bleaching of the hair when it is used in a form of an aqueous formulation additivated with silicones. Other composition-gradient copolymers are described in documents WO 2008/079677, US 2004/180019 and WO 2007/140192.

The present invention sets out to provide novel composition-gradient copolymers.

ACCOUNT OF THE INVENTION

Thus, the invention relates, according to a first subject matter, to composition-gradient copolymers comprising:
repeat units resulting from the polymerization of at least one first monomer $M_1$, the corresponding homopolymer of which exhibits a glass transition temperature $Tg_1$ of less than 20° C., said repeat units representing from 15 to 40% by weight, advantageously from 20 to 35% by weight, with respect to the total weight of the copolymer;
repeat units resulting from the polymerization of at least one second monomer $M_2$, the corresponding homopolymer of which exhibits a glass transition temperature $Tg_2$ of greater than 20° C., said repeat units representing from 45 to 65% by weight, advantageously from 50 to 62% by weight, with respect to the total weight of the copolymer;
hydrophilic repeat units resulting from the polymerization of at least one third monomer $M_3$, said repeat units representing from 10 to 25% by weight, advantageously from 13 to 21% by weight, with respect to the total weight of the copolymer.

It is specified that the term "composition-gradient copolymers" is understood to mean copolymers in which the local composition of monomers changes continuously along a polymer chain, this composition being a function of the reactivity of the monomers which have been brought together. Composition-gradient copolymers are to be distinguished from block copolymers, in which the local composition changes discontinuously along the chain, and they are also to be distinguished from random copolymers, which do not exhibit either the continuous variation in the composition.

$Tg_1$ is between −150° C. and 20° C. and preferably between −120° C. and 15° C.

The glass transition temperatures were measured by differential scanning calorimetry (DSC).

The composition-gradient copolymers of the invention can exhibit a weight-average molecular weight ranging from 30 000 g/mol to 70 000 g/mol, preferably from 40 000 g/mol to 60 000 g/mol, and a polydispersity index of less than 2.

According to the invention, the third monomer $M_3$, which confers the hydrophilic nature on the copolymers of the invention, is advantageously chosen from:
- ethylenic monomers comprising at least one carboxyl group, such as (meth)acrylic acid, itaconic acid or fumaric acid;
- (meth)acrylate monomers comprising at least one polyethylene glycol and/or glycol group optionally substituted on their end functional group by an alkyl, phosphate, phosphonate or sulfonate group;
- ethylenic monomers comprising at least one amide group, such as (meth)acrylamide and their N-substituted derivatives;
- aminoalkyl(meth)acrylate monomers;
- aminoalkyl(meth)acrylamide monomers;
- ethylenic monomers comprising at least one acid anhydride group, such as maleic anhydride or fumaric anhydride;
- vinylamide monomers, such as vinylpyrrolidone or vinylacetamide;
- vinylamine monomers, such as vinylmorpholine or vinylamine;
- vinylpyridine; and
- the mixtures of these.

In particular, the third monomer $M_3$ can be methacrylic acid.

The first monomer $M_1$ is advantageously chosen from alkyl acrylates, the corresponding homopolymer of which exhibits a glass transition temperature of less than 20° C., for example linear or branched $C_1$-$C_{12}$ alkyl acrylates, in particular ethyl acrylate, polyethylene glycol (meth)acrylates and diene monomers, whereas the second monomer $M_2$ is advantageously chosen from styrene monomers, in particular styrene, (meth)acrylate monomers, the corresponding homopolymer of which exhibits a glass transition temperature of greater than 20° C., such as norbornyl acrylate or methyl methacrylate, or (meth)acrylonitrile.

Specific composition-gradient copolymers of the invention are copolymers comprising:
- repeat units resulting from the polymerization of at least one first monomer $M_1$ which is ethyl acrylate, it being possible for said repeat units to represent 32% or 23% by weight, with respect to the total weight of the copolymer;
- repeat units resulting from the polymerization of at least one second monomer $M_2$ which is styrene, it being possible for said repeat units to represent 53% or 60% by weight, with respect to the total weight of the copolymer; and
- hydrophilic repeat units resulting from the polymerization of at least one third monomer $M_3$ which is methacrylic acid, it being possible for said repeat units to represent 15% or 17% by weight, with respect to the total weight of the copolymer.

The composition-gradient copolymers of the invention can be prepared by a process comprising the following stages:
a) a stage of controlled radical polymerization which consists in bringing a mixture of monomers comprising:
- at least one first monomer $M_1$, the corresponding homopolymer of which exhibits a glass transition temperature $Tg_1$ of less than 20° C., said first monomer representing from 15 to 40% by weight, with respect to the total weight of the mixture;
- at least one second monomer $M_2$, the corresponding homopolymer of which exhibits a glass transition temperature $Tg_2$ of greater than 20° C., said second monomer representing from 45 to 65% by weight, with respect to the total weight of the copolymer; and
- at least one third monomer $M_3$ which is hydrophilic or which comprises at least one group capable of being converted into a hydrophilic function group, said third monomer representing from 10 to 25% by weight, with respect to the total weight of the copolymer, into contact with at least one control agent and optionally one polymerization initiator, if the control agent is not capable of initiating a polymerization reaction; and b) optionally a stage of isolation of said copolymer.

More specifically, the polymerization stage a) advantageously takes place under an atmosphere of gas which is inert with regard to the reactants used in a controlled radical polymerization, such as argon or nitrogen, optionally in the presence of an organic solvent intended to dissolve the reactants (monomers, control agent, optionally initiator), it being possible for this organic solvent to be an alkyl acetate, such as butyl acetate or ethyl acetate. It can also be an aromatic solvent, a ketone solvent or an alcohol solvent.

The polymerization stage is carried out at a temperature chosen according to the chemical composition of the mixture of monomers and in particular the kinetic constant for propagation of the monomers and the affinity of the latter for the control agent. This temperature can be chosen in a range extending from 10° C. to 160° C., for example from 25° C. to 130° C. and preferably from 50° C. to 100° C.

During the polymerization stage, the mixture of monomers can be added in one go or continuously over the total duration of the polymerization stage.

The polymerization stage is halted once the desired conversion is achieved, it being known that it is preferable to achieve at least 50% conversion, preferably at least 75% conversion and more preferably still at least 90% conversion.

At the end of the polymerization stage, there may be, if appropriate, a stage of removal of the possible residual monomers, either by evaporation or by addition of an amount of conventional polymerization initiator, such as peroxide or azo derivatives.

Finally, the gradient copolymer obtained can be isolated from its polymerization medium during stage b).

According to the invention, the control agent advantageously corresponds to the following formula (I):

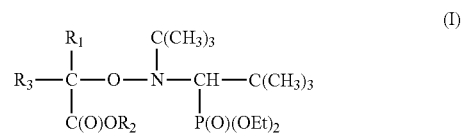

in which:
$R_1$ and $R_3$, which are identical or different, represent a linear or branched alkyl group having a number of carbon atoms ranging from 1 to 3;
$R_2$ represents a hydrogen atom, a linear or branched alkyl group having a number of carbon atoms ranging from 1 to 8, a phenyl group, an alkali metal, such as Li, Na or K, or an ammonium ion, such as $NH_4^+$ or $NHBu_3^+$, $R_1$ and $R_3$ preferably being $CH_3$ and $R_2$ preferably being H.

A specific control agent which can be used to design the gradient copolymers of the invention corresponds to the following formula (II):

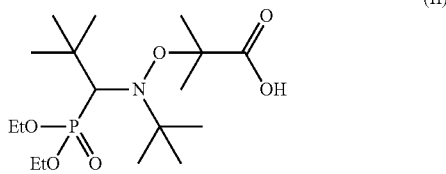

this control agent being denoted under the name BlocBuilder.

The control agent can also be a polyfunctional alkoxyamine corresponding to the following formula (III):

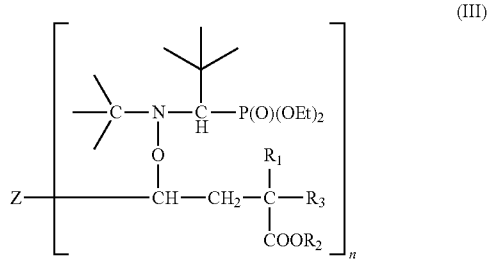

in which:
- $R_1$ and $R_3$, which are identical or different, represent a linear or branched alkyl group having a number of carbon atoms ranging from 1 to 3;
- $R_2$ represents a hydrogen atom, a linear or branched alkyl group having a number of carbon atoms ranging from 1 to 8, a phenyl group, an alkali metal, such as Li, Na or K, or an ammonium ion, such as $NH_4^+$ or $NHBu_3^+$, $R_1$ and $R_3$ preferably being $CH_3$ and $R_2$ preferably being H;
- Z represents an aryl group or a group of formula $Z_1$-[X—C(O)]$_n$, in which $Z_1$ represents a polyfunctional structure originating, for example, from a compound of the polyol type and X is an oxygen atom, a nitrogen atom carrying a carbon-comprising group or a hydrogen atom, or a sulfur atom; and
- n is an integer greater than or equal to 2.

It is specified that the abbreviation Et corresponds to the ethyl group and that the abbreviation Bu corresponds to the butyl group, which can exist in different isomeric forms (n-butyl, sec-butyl or ten-butyl).

A specific example of control agent of the polyfunctional alkoxyamine type in accordance with the general definition given above is the polyfunctional alkoxyamine corresponding to the following formula:

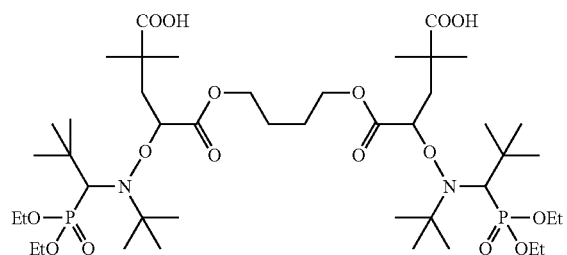 [SMILES: CCOP(=O)(OCC)C(N(OC(CC(C)(C)C(=O)O)C(=O)OCCCCOC(=O)C(CC(C)(C)C(=O)O)ON(C(C(C)(C)C)P(=O)(OCC)OCC)C(C)(C)C)C(C)(C)C)C(C)(C)C]

The choice of the monomers will be dictated by the importance of locating the hydrophilic monomers at a precise point in the chain.

Thus, if it is desired for the hydrophilic units to be in the core of the polymer chain, the choice will preferably be made of a difunctional initiator and of a mixture of monomers such that the reactivity of the hydrophilic monomers is greater than that of the hydrophobic monomers. This is the case, for example, of methacrylic acid with respect to acrylate monomers in general. In the case where it is desired to have hydrophilic units at the periphery, the choice will be made, for example, of the acrylate/vinylpyrrolidone pair.

The gradient copolymers of the invention are water-soluble or water-dispersible. The term "water-soluble copolymer" is conventionally understood to mean a copolymer which can form a clear solution when it is in solution of 5% by weight in water at a temperature of 25° C. The term "water-dispersible copolymer" is understood to mean a copolymer capable of forming, at a content of 5% by weight in water at 25° C., a stable suspension of fine, generally spherical, particles. The mean size of the particles forming said dispersion is less than 1 μm and more generally varies between 5 and 400 nm, preferably from 10 to 250 nm, these mean particles sizes being measured by light scattering.

Therefore, the copolymers can very naturally be placed in aqueous solution.

Thus, the invention relates, according to a third subject matter, to a process for the aqueous dissolution of a gradient copolymer as defined above or capable of being obtained by a process as defined above, comprising the following stages:
- a) dissolving the copolymer in an organic solution comprising a ketone solvent;
- b) optionally neutralizing said solution obtained in a) by addition of a solution of an acid or of a base;
- c) a stage of addition of water or of an aqueous solution to the solution obtained in a) or b);
- d) a stage of evaporation of said organic solution.

Thus, the first stage consists in dissolving the copolymer in an organic solution comprising a ketone solvent, the copolymer being conventionally dissolved in a proportion of a content ranging from 20 to 90% by weight of the total weight of the solution, preferably from 20 to 50%, it being possible for the ketone solvent to be acetone or methyl ethyl ketone.

If need be, the process of the invention comprises a neutralization stage intended to neutralize the acid and/or basic functional groups of the copolymer. More specifically, in the case where the copolymer comprises acidic hydrophilic functional groups, the neutralization stage can consist in adding, to the organic solution comprising the copolymer, a basic solution, preferably of at least 1M, comprising hydroxonium ions $OH^-$, amine compounds, carbonate ions $CO_3^{2-}$ or hydrogencarbonate ions $HCO_3^-$. In the case where the copolymer comprises basic hydrophilic functional groups of the amine type, the neutralization stage can consist in adding, to the organic solution comprising the copolymer, an acid solution, preferably of at least one 1M, such as a solution of hydrochloric acid, hydrobromic acid, hydriodic acid, acetic acid, propionic acid, sulfuric acid, phosphoric acid or hydroboric acid.

In the case where the copolymer comprises solely hydrophilic function groups, such as those resulting from dimethylacrylamide or N-vinylpyrrolidone monomers, the neutralization stage will not be carried out.

After the stage of organic dissolution and the optional neutralization stage, the process comprises a stage of addition of water or, at the very least, of an aqueous solution, advantageously in a proportion such that the copolymer represents from 1 to 80% of the total weight of the solution obtained (organic solution+water/aqueous solution). The aqueous solution, if appropriate, can be a solution comprising water and an alcohol in proportions which can range from 99/1 to 50/50, it being possible for the alcohol to be ethanol and isopropanol.

Finally, the process comprises a stage of evaporation of the organic solvent until the desired concentration of copolymer is obtained. This evaporation stage can consist of a stage of heating at a temperature sufficient for the evaporation of the organic solvent.

The invention also relates to aqueous or organic compositions (or solutions) comprising at least one copolymer as defined above or capable of being obtained by a process as defined above, it being possible for these aqueous or organic compositions, and also the undissolved copolymers of the invention, to be used in the field of paint or adhesive formulations intended in particular to be applied to surfaces having little natural affinity for water or in cosmetic formulations or also in the field of pigment dispersion. In these compositions, the copolymers are advantageously dissolved in water or in a water/alcohol mixture, advantageously at concentrations of greater than or equal to 5% by weight.

The invention will now be described with respect to the following examples, given by way of illustration and without implied limitation.

DETAILED ACCOUNT OF SPECIFIC EMBODIMENTS

In these examples, the molar masses and their distribution (polydispersity index) were determined by steric exclusion chromatography, with universal calibration using polystyrenes as standard and the Mark-Houwink coefficients for PMMA for the copolymers.

The chemical composition of the copolymers can be determined by proton NMR, UV spectrometry or infrared spectrometry.

Example 1

624 g of ethyl acrylate, 729.6 g of styrene, 246.4 g of methacrylic acid, 400 g of methyl ethyl ketone and 14.1 g of BlocBuilder (purity=99%) are introduced at ambient temperature into a 5 liter reactor. The reaction medium is degassed and then heated to 119° C. The temperature is maintained for 200 minutes and then the reaction medium is cooled to ambient temperature. The conversion obtained is 73%. 500 g of methyl ethyl ketone are then added and the polymer solution is then introduced into a devolatilization device in order to remove the solvent and the residual monomers. The polymer is then recovered in the solid form.
The polymer exhibits the following characteristics:

| | |
|---|---|
| % Poly(ethyl acrylate) | 32% by weight |
| % Poly(styrene) | 53% by weight |
| % Poly(methacrylic acid) | 15% by weight |
| Number-average molecular weight (Mn) | 20 840 g/mol |
| Peak molecular weight (Mp) | 51 280 g/mol |
| Weight-average molecular weight (Mw) | 46 500 g/mol |
| Polydispersity Index (PI) | 1.9 |

Example 2

404 g of ethyl acrylate, 928 g of styrene, 272 g of methacrylic acid, 400 g of methyl ethyl ketone and 14.2 g of BlocBuilder (purity=99%) are introduced at ambient temperature into a 5 liter reactor. The reaction medium is degassed and then heated to 119° C. The temperature is maintained for 255 minutes and then the reaction medium is cooled to ambient temperature. The conversion obtained is 73%. 500 g of methyl ethyl ketone are then added and the polymer solution is then introduced into a devolatilization device in order to remove the solvent and the residual monomers. The polymer is then recovered in the solid form.
The polymer exhibits the following characteristics:

| | |
|---|---|
| % Poly(ethyl acrylate) | 23% by weight |
| % Poly(styrene) | 60% by weight |
| % Poly(methacrylic acid) | 17% by weight |
| Number-average molecular weight (Mn) | 22 390 g/mol |
| Peak molecular weight (Mp) | 51 680 g/mol |
| Weight-average molecular weight (Mw) | 47 330 g/mol |
| Polydispersity Index (PI) | 1.9 |

What is claimed is:

1. A gradient copolymer composition, comprising a gradient copolymer comprising:
   repeat units resulting from the polymerization of at least one first monomer $M_1$, the corresponding homopolymer of which exhibits a glass transition temperature $Tg_1$ of less than 20° C., said repeat units representing from 15 to 40% by weight, with respect to the total weight of the copolymer;
   repeat units resulting from the polymerization of at least one second monomer $M_2$, the corresponding homopolymer of which exhibits a glass transition temperature $Tg_2$ of greater than 20° C., said repeat units representing from 45 to 65% by weight, with respect to the total weight of the copolymer;
   hydrophilic repeat units resulting from the polymerization of at least one third monomer $M_3$, said repeat units representing from 10 to 25% by weight, with respect to the total weight of the copolymer.

2. The gradient copolymer composition as claimed in claim 1, in which said repeat units resulting from the polymerization of the first monomer $M_1$ represent from 20 to 35% by weight, with respect to the total weight of the copolymer.

3. The gradient copolymer composition claimed in claim 1, in which said repeat units resulting from polymerization of the second monomer $M_2$ represent from 50 to 62% by weight, with respect to the total weight of the copolymer.

4. The gradient copolymer composition as claimed in claim 1, in which said repeat units resulting from the polymerization of the third monomer $M_3$ represent from 13 to 21% by weight, with respect to the total weight of the copolymer.

5. The gradient copolymer composition as claimed in claim 1, in which $Tg_1$ is between −150° C. and 20° C.

6. The gradient copolymer composition as claimed in claim 1, exhibiting a weight-average molecular weight ranging from 10 000 g/mol to 70 000 g/mol, and a polydispersity index of less than 2.

7. The gradient copolymer composition as claimed in claim 1, in which the third monomer $M_3$ is selected from the group consisting of
   ethylenic monomers comprising at least one carboxyl group, (meth)acrylic acid, itaconic acid, fumaric acid;
   (meth)acrylate monomers comprising at least one polyethylene glycol and/or glycol group optionally substituted on their end functional group by an alkyl, phosphate, phosphonate or sulfonate group;
   ethylenic monomers comprising at least one amide group, (meth)acrylamide and their N-substituted derivatives;
   aminoalkyl (meth)acrylate monomers;

amino alkyl(meth)acrylamide monomers;
ethylenic monomers comprising at least one acid anhydride group, maleic anhydride, fumaric anhydride;
vinylamide monomers, vinylpyrrolidone, vinylacetamide;
vinylamine monomers, vinylmorpholine, vinylamine;
vinylpyridine; and
the mixtures of these.

8. The gradient copolymer composition as claimed in claim 1, in which the first monomer $M_1$ is chosen from alkyl acrylates, the corresponding homopolymer of which exhibits a glass transition temperature of less than 20° C., polyethylene glycol (meth)acrylates or diene monomers.

9. The gradient copolymer composition as claimed in claim 1, in which the second monomer $M_2$ is chosen from styrenemonomers, (meth)acrylate monomers, the corresponding homopolymer of which exhibits a glass transition temperature of greater than 20° C., or (meth)acrylonitrile.

10. The gradient copolymer composition as claimed in claim 1, which is a copolymer comprising:
repeat units resulting from the polymerization of at least one first monomer $M_1$ which is ethyl acrylate, representing 32% to 23% by weight, with respect to the total weight of the copolymer;
repeat units resulting from the polymerization of at least one second monomer $M_2$ which is styrene, representing 53% to 60% by weight, with respect to the total weight of the copolymer, and
hydrophilic repeat units resulting from the polymerization of at least one third monomer $M_3$ which methacrylic acid, representing 15% to 17% by weight, with respect to the total weight of the copolymer.

11. A process for the preparation of the gradient copolymer composition as defined in claim 1, comprising the following stages:
a) bringing a mixture of monomers into contact with at least one control agent and optionally one polymerization initiator, if the control agent is not capable of initiating a polymerization reaction in a controlled radical polymerization stage wherein said mixture of monomers comprises:
at least one first monomer $M_1$, the corresponding homopolymer of which exhibits a glass transition temperature $Tg_1$ of less than 20° C., said first monomer representing from 15 to 40% by weight, with respect to the total weight of the mixture;
at least one second monomer $M_2$, the corresponding homopolymer of which exhibits a glass transition temperature $Tg_2$ of greater than 20° C., said second monomer representing from 45 to 65% by weight, with respect to the total weight of the copolymer; and
at least one third monomer $M_3$ which is hydrophilic or which comprises at least one group capable of being converted into a hydrophilic function group, said third monomer representing from 10 to 25% by weight, with respect to the total weight of the copolymer,
b) optionally a stage of isolation of said copolymer.

12. The preparation process as claimed in claim 11, in which the control agent is chosen from the compounds of formulae (I), (II), and (III):

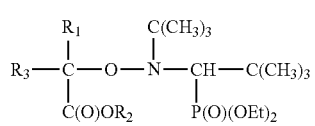

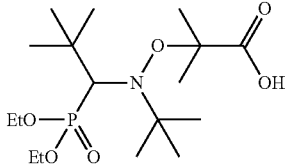

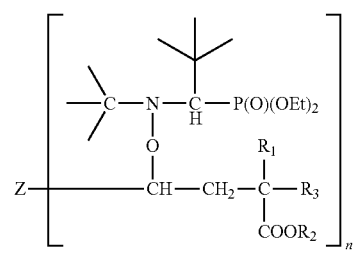

in which:
$R_1$ and $R_3$, Which are identical or different, represent a linear or branched alkyl group having a number of carbon atoms ranging from 1 to 3;
$R_2$ represents a hydrogen atom, a linear or branched alkyl group having a number of carbon atoms ranging from 1 to 8, a phenyl group, an alkali metal or an ammonium ion;
Z represents an aryl group or a group of formula $Z_1$—[X—C(O)]$_n$, in which $Z_1$ represents a polyfunctional structure and X is an oxygen atom, a nitrogen atom carrying a carbon-comprising group or a hydrogen atom, or a sulfur atom; and
n is an integer greater than or equal to 2.

13. The preparation process as claimed in claim 11, in which the polymerization stage is carried out at a temperature ranging from 10° C. to 160° C.

14. A process for the aqueous dissolution of a gradient copolymer as defined in claim 1, comprising the following stages:
a) dissolving the copolymer in an organic solution comprising a ketone solvent;
b) optionally neutralizing said solution obtained in a) by addition of a solution of an acid or of a base;
c) adding water or of an aqueous solution to the solution obtained in a) or b);
d) evaporating said organic solution.

15. The gradient copolymer composition of claim 1 wherein comprising 5% by weight or greater of said gradient copolymer in an aqueous or organic solvent.

16. The gradient copolymer composition of claim 15 comprising a paint, adhesive formulations, cosmetic formulations or pigment dispersion.

17. The gradient copolymer composition as claimed in claim 5, in which $Tg_1$ is between −120° C. and 15° C.

18. The gradient copolymer composition as claimed in claim 6, exhibiting a weight-average molecular weight ranging from 40 000 g/mol to 60 000 g/mol.

19. The preparation process of claim 12, wherein $Z_1$ represents a polyfunctional structure originating from a polyol compound.

* * * * *